US010238409B2

(12) United States Patent
Mire et al.

(10) Patent No.: US 10,238,409 B2
(45) Date of Patent: *Mar. 26, 2019

(54) SURGICAL ASSEMBLY WITH FLEXIBLE ARM

(71) Applicant: WARSAW ORTHOPEDIC INC., Warsaw, IN (US)

(72) Inventors: David A. Mire, Cordova, TN (US); Kelli C. Armstrong, Arlington, TN (US); Paul F. Wheeler, Hernando, MS (US); David L. Fiorella, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 169 days.

This patent is subject to a terminal disclaimer.

(21) Appl. No.: 15/220,819

(22) Filed: Jul. 27, 2016

(65) Prior Publication Data

US 2016/0331392 A1    Nov. 17, 2016

Related U.S. Application Data

(63) Continuation of application No. 12/832,598, filed on Jul. 8, 2010, now Pat. No. 9,486,296.

(51) Int. Cl.
*A61B 17/29* (2006.01)
*A61B 17/02* (2006.01)
*A61B 90/50* (2016.01)
*A61B 17/00* (2006.01)

(52) U.S. Cl.
CPC ........ *A61B 17/29* (2013.01); *A61B 17/00234* (2013.01); *A61B 17/02* (2013.01); *A61B 90/50* (2016.02); *A61B 2017/0042* (2013.01); *A61B 2017/0069* (2013.01); *A61B 2017/00407* (2013.01); *A61B 2017/2908* (2013.01); *A61B 2090/508* (2016.02)

(58) Field of Classification Search
CPC . A61F 2/966; A61F 2/958; A61F 2/04; A61B 17/29; A61B 90/50
See application file for complete search history.

(56) References Cited

U.S. PATENT DOCUMENTS

| 3,858,578 A | | 1/1975 | Milo | |
|---|---|---|---|---|
| 4,151,840 A | * | 5/1979 | Barrington | 600/40 |
| 4,353,358 A | * | 10/1982 | Emerson | 600/139 |
| 5,513,827 A | | 5/1996 | Michelson | |

(Continued)

FOREIGN PATENT DOCUMENTS

| DE | 29801807 U1 | 11/1998 |
|---|---|---|
| WO | 9849944 A1 | 11/1998 |

*Primary Examiner* — Richard Louis (57) ABSTRACT

A surgical assembly includes a tensioner having a first end and a second end. A tension member extends from the first end of the tensioner. A mounting member is connected to the second end of the tensioner. An arm extends from the first end of the tensioner and includes a series of relatively moveable links that define an axial bore configured for disposal of the tension member. Each link defines a first mating surface and a second mating surface disposed in a configuration such that tensioning of the tension member interlocks the first mating surface with the second mating surface of an adjacent link in the series to selectively fix the links in a selected orientation.

20 Claims, 7 Drawing Sheets

(56) References Cited

U.S. PATENT DOCUMENTS

| | | | |
|---|---|---|---|
| 5,522,788 A * | 6/1996 | Kuzmak | A61B 17/00234 600/141 |
| 5,522,827 A * | 6/1996 | Combs et al. | 606/167 |
| 5,603,723 A * | 2/1997 | Aranyi et al. | 606/205 |
| 5,632,717 A * | 5/1997 | Yoon | 600/106 |
| 5,636,815 A * | 6/1997 | Wilson | 248/125.9 |
| 5,662,300 A | 9/1997 | Michelson | |
| 5,766,196 A * | 6/1998 | Griffiths | 606/170 |
| 5,830,231 A * | 11/1998 | Geiges, Jr. | 606/205 |
| 5,899,425 A * | 5/1999 | Corey, Jr. et al. | 248/276.1 |
| 6,439,429 B1 * | 8/2002 | Gross | 222/92 |
| 6,439,439 B1 * | 8/2002 | Rickard et al. | 222/391 |
| 6,461,363 B1 * | 10/2002 | Gadberry | A61B 17/122 606/139 |
| 6,464,629 B1 | 10/2002 | Boone et al. | |
| 6,688,564 B2 | 2/2004 | Salvermoser et al. | |
| 6,758,808 B2 * | 7/2004 | Paul et al. | 600/229 |
| 6,767,153 B1 | 7/2004 | Holbrook | |
| 6,860,668 B2 | 3/2005 | Ibrahim et al. | |
| 9,486,296 B2 * | 11/2016 | Mire | A61B 17/02 |
| 2001/0025905 A1 | 10/2001 | Carpenter et al. | |
| 2003/0036748 A1 * | 2/2003 | Cooper et al. | 606/1 |
| 2003/0083596 A1 * | 5/2003 | Kramer et al. | 600/595 |
| 2003/0089831 A1 | 5/2003 | Salvermoser et al. | |
| 2003/0165352 A1 | 9/2003 | Ibrahim et al. | |
| 2003/0216619 A1 | 11/2003 | Scirica et al. | |
| 2004/0138525 A1 * | 7/2004 | Saadat et al. | 600/104 |
| 2004/0242969 A1 * | 12/2004 | Sherts et al. | 600/231 |
| 2005/0070764 A1 * | 3/2005 | Nobis | A61B 1/0052 600/131 |
| 2005/0131457 A1 | 6/2005 | Douglas et al. | |
| 2005/0152739 A1 | 7/2005 | Ibrahim et al. | |
| 2005/0197536 A1 * | 9/2005 | Banik et al. | 600/179 |
| 2005/0226682 A1 * | 10/2005 | Chersky | F16M 11/14 403/56 |
| 2005/0250990 A1 * | 11/2005 | Le et al. | 600/114 |
| 2006/0084831 A1 * | 4/2006 | Zhang | 585/670 |
| 2006/0094931 A1 * | 5/2006 | Danitz | A61B 1/0055 600/141 |
| 2008/0121765 A1 * | 5/2008 | Fetzer | A61B 90/50 248/122.1 |
| 2008/0243106 A1 * | 10/2008 | Coe | A61B 17/00234 606/1 |
| 2009/0228007 A1 * | 9/2009 | Justin et al. | 606/62 |

\* cited by examiner

FIG. 20

SURGICAL ASSEMBLY WITH FLEXIBLE ARM

CROSS REFERENCE TO RELATED APPLICATIONS

This application is a continuation of U.S. patent application Ser. No. 12/832,598, filed on Jul. 8, 2010, which is expressly incorporated herein by reference, in its entirety.

TECHNICAL FIELD

The present disclosure generally relates to medical devices, systems and methods employed during surgical applications, and more particularly, to a surgical assembly that includes a series of interlocking links configured to support a surgical instrument, which is used, for example, with a minimally invasive surgical procedure.

BACKGROUND

Invasive surgical procedures such as open surgery for pathologies located within the body can cause significant trauma to intervening tissues. These procedures often require that the skin, tissue and/or vessels surrounding a surgical site be cut, removed, and/or repositioned so that a surgeon can access the site within the body. This trauma to the body may result in damage and scarring, as well as infection and long recovery.

Percutaneous minimally invasive surgical procedures are known that have attempted to overcome the above drawbacks of open surgery. Minimally invasive surgical procedures minimize disruption and trauma to the body to reduce recovery time and post-operative pain. For example, minimally invasive surgical techniques are employed for spinal and neurosurgical applications to access surgical sites within the body adjacent vital intervening tissues, in an effort to avoid damaging such vital tissues. Surgical retractors, mounting assemblies and other instruments are used in such minimally invasive procedures to increase the workspace of the minimally invasive surgical incision and adjacent areas used to access a surgical site. This disclosure describes an improvement over these prior art technologies.

SUMMARY OF THE INVENTION

Accordingly, a surgical assembly, system and related methods are provided for employment during surgical applications. It is contemplated that the surgical assembly includes a series of interlocking links configured to support a surgical instrument and is used, for example, with a minimally invasive surgical procedure.

In one particular embodiment, in accordance with the principles of the present disclosure, a surgical assembly is provided. The surgical assembly includes a tensioner having a first end and a second end. A tension member extends from the first end of the tensioner. A mounting member is connected to the second end of the tensioner. An arm extends from the first end of the tensioner and includes a series of relatively moveable links that define an axial bore configured for disposal of the tension member. Each link defines a first mating surface and a second mating surface disposed in a configuration such that tensioning of the tension member interlocks the first mating surface with the second mating surface of an adjacent link in the series to selectively fix the links in a selected orientation.

In one embodiment, the surgical assembly includes a tensioner having a first end, a second end and a body. The second end includes a slide connected with the body. A cable is connected with the body and extends from the first end of the tensioner. A mounting member is connected with the body of the tensioner. An arm includes a series of relatively movable links that define an axial bore configured for disposal of the cable. Each link further defines a first mating surface and an opposing second mating surface. The mating surfaces include interlocking teeth disposed in a configuration such that engagement of the slide relative to the body selectively tensions the cable via engagement of the links and the first mating surface interlocks with the second mating surface of an adjacent link in the series to selectively fix the links in a selected orientation.

In one embodiment, the surgical assembly includes a pistol-grip tensioner having a body. A slide is connected to the body. A ratchet mechanism is connected to the body with the slide. A cable is connected with the body. A mounting member is connected with the body. A proximal link has a first end including a mating surface and a second end mounted with the body. A series of relatively movable links define an axial bore configured for disposal of the cable. Each link further defines a first mating surface and a second mating surface. Each link is movable relative to an adjacent link through an angular range in a single plane only. The mating surface of the proximal link is configured to interlock with the first mating surface. A distal link has a mating surface configured to interlock with the second mating surface and an end for releasably engaging an instrument. Engagement of the slide relative to the body selectively tensions the cable via engagement of the links and the first mating surface interlocks with the second mating surface of an adjacent link in the series to selectively fix the links in a selected orientation via fixation of the ratchet mechanism with the body.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

The exemplary embodiments of the surgical assembly, related systems and methods of use disclosed are discussed in terms of medical devices employed during surgical applications and more particularly, in terms of a surgical assembly that includes a series of interlocking links configured to support a surgical instrument, which is used, for example, with a minimally invasive surgical procedure. It is envisioned that the surgical assembly, systems and methods of use disclosed provide a reliable and user-friendly mount and positioning assembly with an interlocking geometry of links, which is low profile to a patient allowing a surgeon facile access to a surgical site. It is further envisioned that the surgical assembly is adjustable without requiring the use of several knob/button devices.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical assembly may be employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may be employed with procedures for treating the lumbar, cervical, thoracic and pelvic regions of a spinal column. The system and methods of the present disclosure may also be used on animals, bone models and other non-living substrates, such as for training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of a surgical assembly, related components and exemplary methods of employing the surgical assembly in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a surgical assembly 20 in accordance with the principles of the present disclosure.

The components of surgical assembly 20 and related systems are fabricated from materials suitable for medical applications, including metals, polymers, ceramics, biocompatible materials and/or their composites, depending on the particular application and/or preference of a medical practitioner. For example, the components of the surgical assembly, individually or collectively, can be fabricated from materials such as stainless steel, titanium, thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, biocompatible materials such as polymers including plastics, metals, ceramics and composites thereof, rigid polymers including polyphenylene, polyamide, polyimide, polyetherimide, polyethylene, epoxy, and various components of the surgical assembly may have material composites, including the above materials, to achieve various desired characteristics such as strength, rigidity, elasticity, compliance, biomechanical performance, durability and radiolucency or imaging preference.

Figure 1:
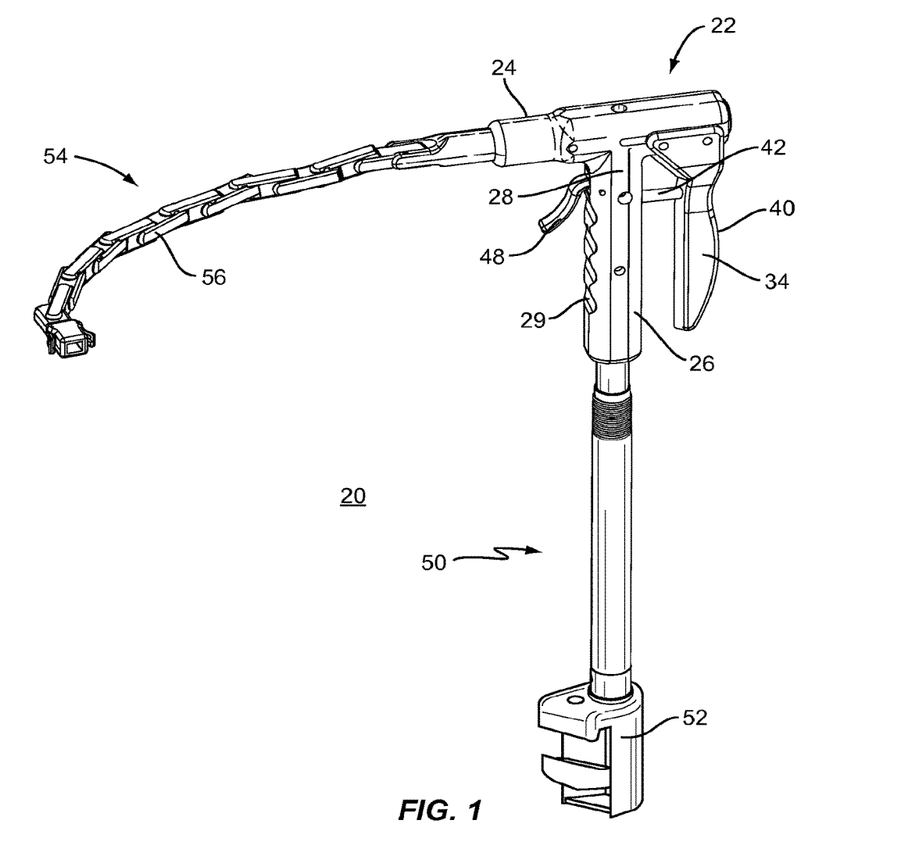
FIG. 1 is a perspective view of one particular embodiment of a surgical assembly in accordance with the principles of the present disclosure.
Figure 2:
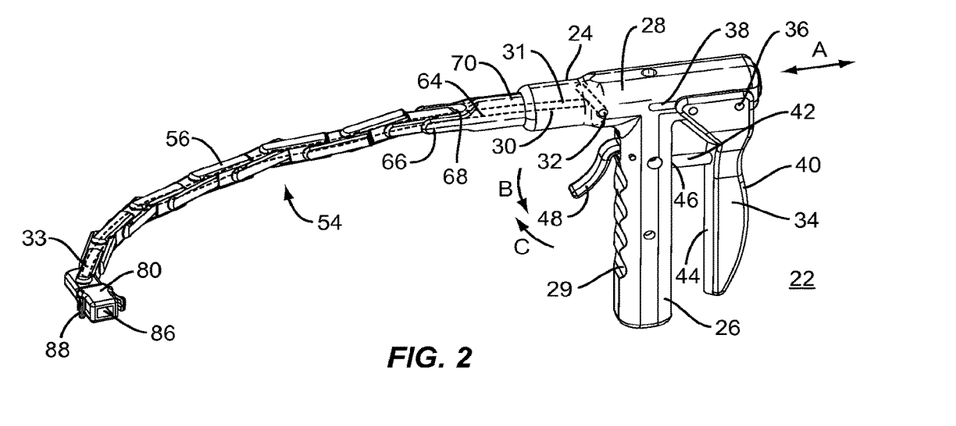
FIG. 2 is a perspective view of a tensioner and an arm of the surgical assembly shown in FIG. 1.

Surgical assembly 20 includes a tensioner 22 having a first end 24, a second end 26 and a body 28. Body 28 has a pistol grip configuration and second end 26 defines finger grips 29 to facilitate handling and manipulation of tensioner 22 by a practitioner. It is contemplated that tensioner 22 may be monolithically formed or integrally assembled. Body 28 has a cylindrical configuration and defines an interior cavity for support of various components, as will be described.

A tension member, such as, for example, a cable 30 extends from first end 24. Cable 30 has a first end 31 attached to a pin 32 of body 28 and extends therefrom to a distal end 33 through the interlocking links. Cable 30 is elastic and has a tension, which can be increased or decreased to facilitate support and positioning of a surgical instrument(s). It is envisioned that cable 30 has a band configuration. It is further envisioned that cable 30 may have other configurations, such as, for example, a wire rope with a twisted helix.

Tensioner 22 includes a first member, such as, for example, a slide 34 that is relatively movable from body 28. Slide 34 is connected to body 28 with pins 36 that extend into body 28 through slots 38, which are disposed on opposing sides of body 28. Slide 34 has a handle grip configuration and is designed for manipulation for tensioning cable 30. Slide 34 has a user contoured surface 40 that upon engagement causes axial movement of slide 34, in the direction shown by arrows A in FIG. 2, as facilitated by movement of pins 36 along slot 38.

Slide 34 includes an internal member extending axially along the interior cavity of body 28 to engage a proximal end of the interlocking links. As the internal member of slide 34 engages the proximal end of the interlocking links, the proximal end of the interlocking links are urged/forced in the direction of arrows A according to the manipulation of slide 34. This engagement increases or decreases, depending on the direction of manipulation and/or the magnitude of force applied to slide 34 along arrows A, the tension of cable 30 due to the connection of cable 30 with body 28 and distal end 33 of the interlocking links, as will be described. As tension is applied to proximal end 31 relative to the proximal end of the links, the distal end of the links is pulled towards the proximal link forcing the links together. It is envisioned that tensioner 22 may include alternative first members to tension cable 30, such as, for example, a side projecting slide bolt.

Slide 34 is releasably locked to a fixed position with body 28 via a ratchet mechanism 42. Ratchet mechanism 42 extends from a front surface 44 of slide 34 and passes through a slot 46 of body 28. Body 28 is selectively fixable with ratchet mechanism 42 during relative movement of slide 34. Ratchet mechanism 42 is a rack with serrations that engage or mesh with reciprocal grooves in slot 46 to selectively fix the tension of cable 30. As slide 34 moves in the direction of arrows A, the tension of cable 30 is increased or decreased. Upon movement of slide 34 to a selected tension of cable 30, body 28 is selectively fixed with ratchet mechanism 42.

Tensioner 22 includes a second member, such as, for example, a trigger 48 that is engageable to selectively fix body 28 with ratchet mechanism 42 at a selected tension of cable 30. Trigger 48 can be manipulated, in the direction shown by arrow C in FIG. 2, to lock ratchet mechanism 42 with slot 46 at a selected tension of cable 30. Trigger 48 is pivotable relative to body 28 and is depressed, in the direction shown by arrow B in FIG. 2, to disengage ratchet mechanism 42 from slot 46 and release cable 30 from the selected tension. It is contemplated that tension of cable 30 may be selectively fixed via free manipulation, and not require a locking element. It is further contemplated that a first tension of cable 30 may be selected and locked, and then released from that tension and a second tension selected and locked such that the tension of cable 30 can be adjusted during a surgical procedure. Cable 30 may be adjusted to one or a plurality of tensions during a surgical procedure.

A mounting member 50 is connected to second end 26. Mounting member 50 has an adjustable clamp 52 configured for mounting with a fixture, such as, for example, a bed rail (not shown). It is contemplated that mounting can be performed from a sterile field after a patient has been draped.

Figure 3:
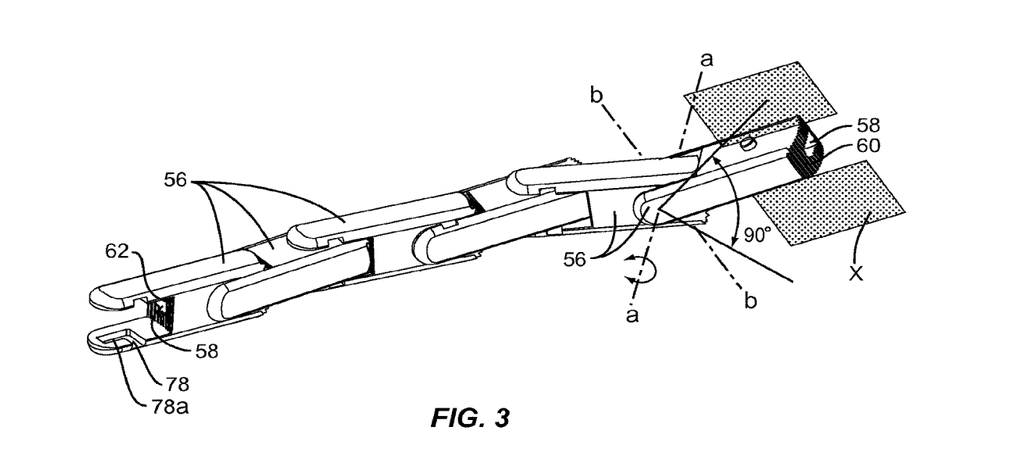
FIG. 3 is an enlarged perspective view of links shown in FIG. 1.

An arm 54 extends from first end 24 and includes a series of relatively movable links 56 that define an axial bore 58 configured for disposal of cable 30. Axial bore 58 has an oval cross section configuration. It is envisioned that bore 58 may have alternative cross section geometries, such as, for example, circular, polygonal, uniform, non-uniform and/or alternate or changing diameter. Each link 56 defines a first mating surface 60 and an opposing second mating surface 62, the mating surfaces being configured to interlock with a reciprocal mating surface of an adjacent link 56 in the series of links for support and positioning of an instrument, as will be described. Axial bore 58 extends through mating surfaces 60,62 for disposal of cable 30. It is contemplated that cable 30 is threaded with links 56.

A proximal link 64 has a first end 66 including a mating surface 68 configured to interlock, similar to that described herein, with first mating surface 60 and a second end 70 mounted with first end 24. First end 66 also connects to link 56 via a pin/slot attachment for relative rotation of the links prior to fixation, as described below.

Cable 30 extends from pin 32 through proximal link 64 and into links 56. Second end 70 is engageable with the internal member of slide 34 and proximal link 64 is movable and connected with the series of links 56, as described above, to tension cable 30. It is contemplated that proximal link 64 is axially movable and rotatable relative to first end 24 of body 28 to facilitate positioning of the instrument. It is further contemplated that proximal link 64 may be non-rotatable.

Figures 4, 5:
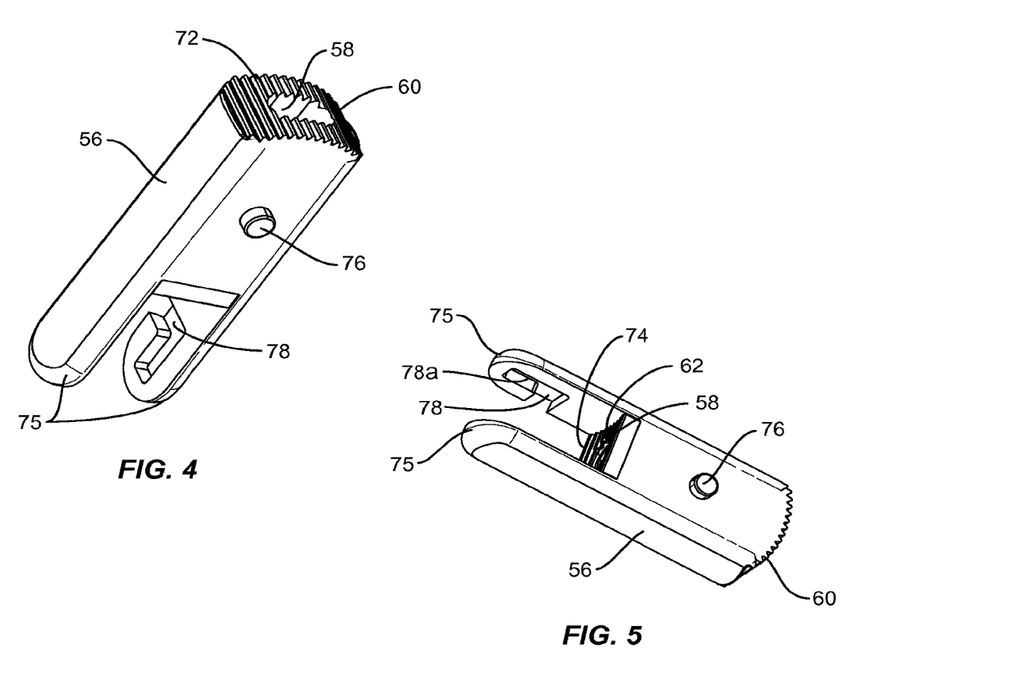
FIG. 4 is an enlarged perspective view of a link shown in FIG. 1.
FIG. 5 is an enlarged perspective view of a link shown in FIG. 1.

Mating surface 60 includes a plurality of teeth 72 and adjacent grooves that interlock with a plurality of teeth 74 and adjacent grooves of mating surface 62. As slide 34 is manipulated or squeezed relative to body 28, the internal member of slide 34 engages proximal link 64 such that interlocking teeth 72,74 mesh and become disposed in a configuration to selectively tension cable 30 via engagement of links 56, which tighten. As the tension of cable 30 is increased, first mating surface 60 interlocks with second mating surface 62 of an adjacent link 56 in the series to selectively fix links 56 in a selected orientation.

Teeth 72, 74 become disposed in the grooves of the opposing mating surface to selectively fix a link 56 and an adjacent link 56 in a particular relative orientation such that arm 54 and surgical assembly 20 support an instrument in a position relative to a surgical site, according to the requirements of a particular application. It is envisioned that surgical assembly 20 may position an instrument in one or a plurality of orientations relative to a surgical site, and that arm 54 can be flexed in a plurality of orientations such as, multi-axial, linear, arcuate, helical and perpendicular and then fixed for orientation of an instrument. It is envisioned that the mating surfaces may be knurled, textured, form a friction or pressure fit engagement, notch and groove, single tooth and groove and/or include separate mechanical fixation such as a clamp. Upon interlocking fixation, it is envisioned that links 56 are configured to prevent undesired rotation of link joints and twisting of cable 30.

Mating surface 60 has a convex configuration and mating surface 62 has a concave configuration to facilitate interlocking fixation of surfaces 60,62. Each link 56 includes extensions 75 configured to support an adjacent link 56. Each link 56 has a pin 76 configured for receipt within a slot 78 formed in extensions 75 of an adjacent link 56. Disposal of pin 76 within slot 78 facilitates attachment of links 56 and hinged movement such that links 56 are relatively rotatable and/or pivotable, as will be described, for fixation of arm 54 in a preselected orientation. Slot 78 includes an axial channel 78a that is configured for movement of pin 76 therein. During flexing of arm 54, pin 76 is freely movable within channel 78a. As slide 34 is manipulated to tension cable 30 and fix links 56 in a selected orientation, links 56 tighten and pin 76 is drawn deeper into channel 78a for fixation. Upon release of tension on cable 30, as described above, pin 76 can again freely move in channel 78a.

Prior to interlocking fixation, link 56 is movable relative to an adjacent link 56 through an angle in a single plane only to provide reliability in operation and fixation of mating parts. Mating surface 60 is elongated along a first axis, such as, for example, axis a and a first mating surface 60 of an adjacent link 56 is elongated along a second axis, such as, for example, axis b. Axis a is oriented transverse to axis b. Each link 56 is movable relative to an adjacent link 56 through an angular range in a single plane only, such as, for example, a plane x. It is contemplated that each link 56 is movable relative to an adjacent link 56 through an angular range of 90 degrees. It is contemplated that links 56 may alternatively be relatively movable in one or a plurality of planes, directions and/or degrees of freedom, may be rotatable or twisted and/or axially movable.

Figure 6:
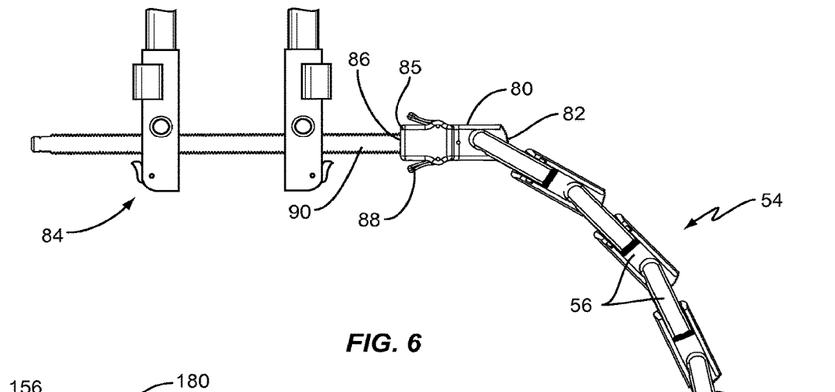
FIG. 6 is a cutaway top view of the surgical assembly shown in FIG. 1 connected to an instrument.
Figure 7:
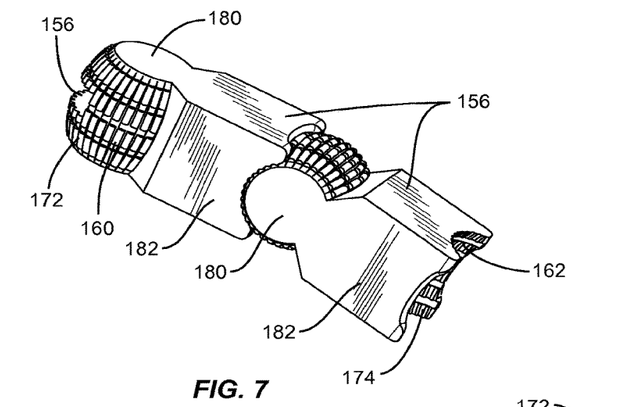
FIG. 7 is a perspective view of one embodiment of the links shown in FIG. 3.
Figure 8:
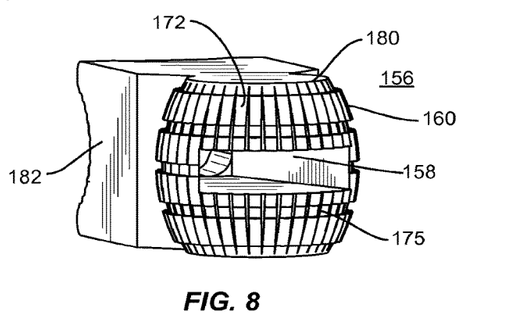
FIG. 8 is an enlarged perspective view of a link shown in FIG. 7.
Figure 9:
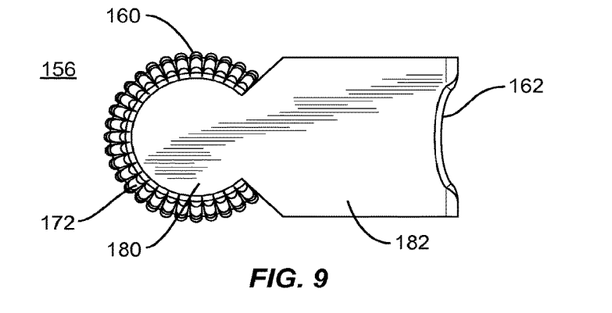
FIG. 9 is an enlarged plan view of the link shown in FIG. 7.
Figure 10:
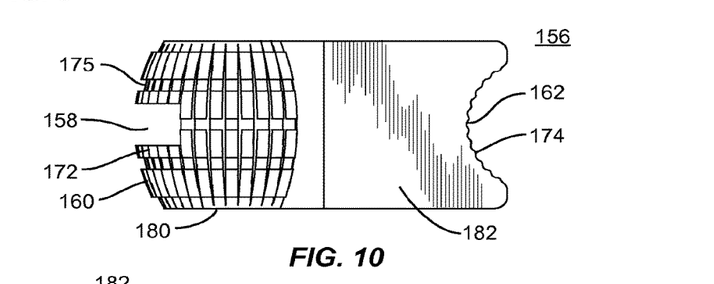
FIG. 10 is an enlarged side view of the link shown in FIG. 7.
Figure 11:
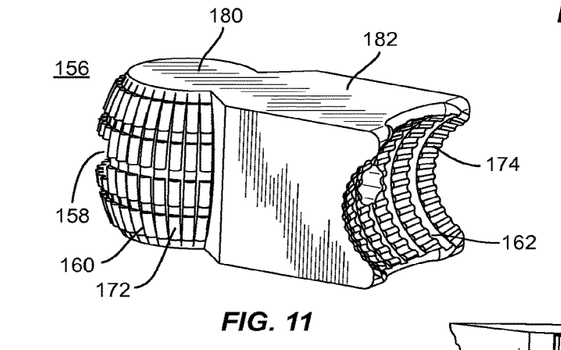
FIG. 11 is a perspective view of the link shown in FIG. 7.
Figure 12:
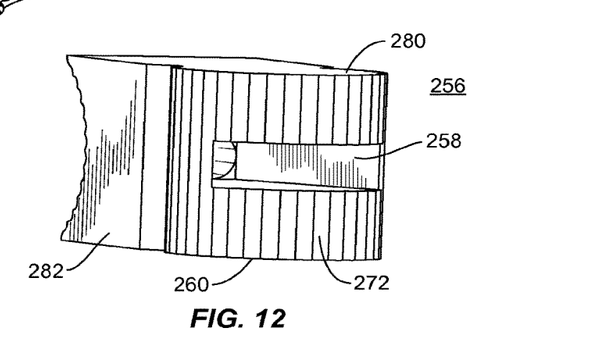
FIG. 12 is a perspective view of one embodiment of the link shown in FIG. 4.
Figure 13:
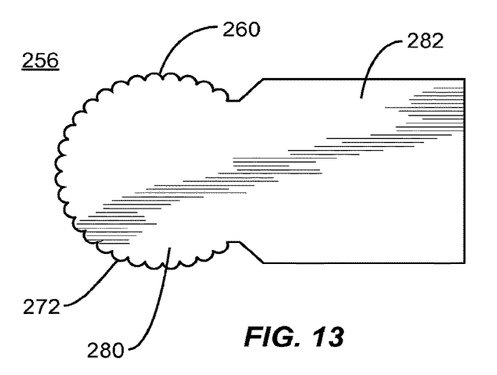
FIG. 13 is a plan view of the link shown in FIG. 12.
Figure 14:
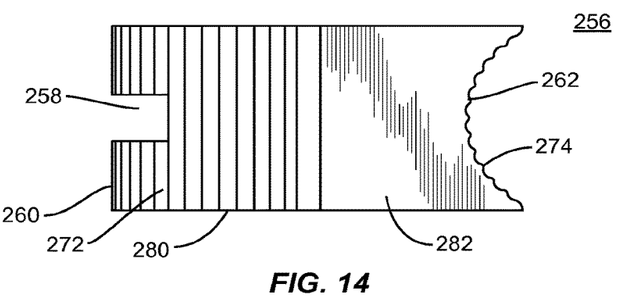
FIG. 14 is a side view of the link shown in FIG. 12.
Figure 15:
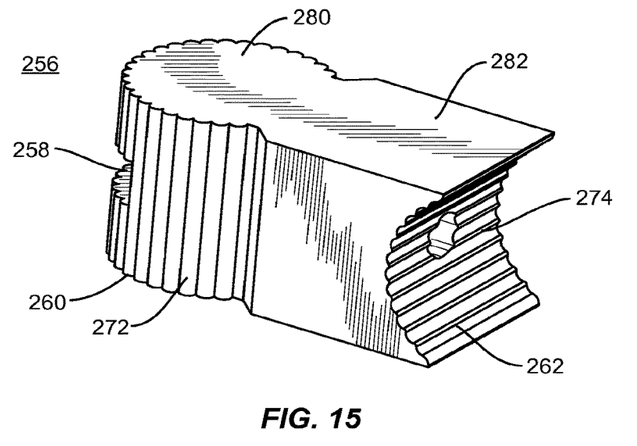
FIG. 15 is a perspective view of the link shown in FIG. 12.

A distal link 80 has a mating surface 82 configured to interlock, similar to that described herein, with second mating surface 62 and an end 85 for releasably engaging an instrument, such as, for example, a retractor assembly 84. End 85 defines a cavity 86 for receiving retractor assembly 84 and a pair of pawls 88 for releasably retaining retractor assembly 84 within cavity 86. Retractor assembly 84 includes a bar 90 having grooves (not shown) that are inserted within cavity 86. For connection of retractor assembly 84 with surgical assembly 20, bar 90 is inserted within cavity 86, which causes pawls 88 to become disposed within the grooves such that distal link 80 releasably retains retractor assembly 84. To disengage retractor assembly 84 from surgical assembly 20, pawls 88 are engaged inwardly to cause a portion of pawls 88 to pivot outwardly such that pawls 88 are released from the grooves such that bar 90 is removable from cavity 86.

In assembly, operation and use, the surgical system including surgical assembly 20 is employed, for example, with a minimally invasive surgical procedure for spinal and neurosurgical applications with a patient. For example, during minimally invasive spine surgery, a surgeon will make a small incision, typically less than one inch, in the skin of a patient's back over vertebrae to be treated. One or more dilators may be employed to gradually separate the muscles and create a portal through which the surgery may be performed.

Mounting member 50 of surgical assembly 20 is mounted to a bed rail, or other fixture. Retractor assembly 84 is attached to arm 54, as described above, and surgical assembly 20 with retractor assembly 84 is positioned adjacent the surgical site over the small incision described above. As facilitated by the configuration of surgical assembly 20, retractor assembly 84 may be positioned, repositioned and/or adjusted, to one or a plurality of orientations.

It is envisioned that the use of microsurgical and image guided technologies may be employed to access, view and repair spinal deterioration or damage, with the aid of surgical assembly 20. Upon completion of the procedure, the surgical instruments and assemblies are removed and the incision is closed. Alternatively, surgical assembly 20 may employed with an open spine surgery, which may involve making a long incision down the back, stripping large bands of muscle away from the spine and using retractor assembly 84 to retract, or pull the surrounding tissues and muscles to create a surgical site for treatment. It is envisioned that surgical assembly 20 may also be employed with mini-open surgery and percutaneous surgical implantation.

It is contemplated that a surgical procedure may employ other instruments that can be mounted with surgical assembly 20, such as, for example, nerve root retractors, tissue retractors, forceps, cutter, drills, scrapers, reamers, separators, rongeurs, taps, cauterization instruments, irrigation and/or aspiration instruments, illumination instruments and/or inserter instruments.

Surgical assembly 20 may be employed for performing spinal surgeries, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

In one embodiment, as shown in FIGS. 7-11, arm 54 of surgical assembly 20, similar to that described above, includes a series of relatively movable links 156. Link 156 has a first end 180 having a barrel configuration and a second end 182 having a block configuration. Links 156 define an axial bore 158 configured for disposal of cable 30. Axial bore 158 is formed with each link 156 and has a rectangular configuration therethrough that decreases in width from first end 180 to second end 182. First end 180 defines a first mating surface 160 and second end 182 defines an opposing second mating surface 162, the mating surfaces being configured to interlock with a reciprocal mating surface of an adjacent link 156 in the series of links for support and positioning of an instrument, as described above. Axial bore 158 extends through mating surfaces 160,162 for disposal of cable 30.

Mating surfaces 160,162 include a plurality of teeth 172,174 and adjacent grooves disposed arcuately about the barrel surface that interlock, similar to that described above. Teeth 172, 174 are disposed in parallel rows about mating surfaces 160,162, and are spaced apart by channels 175. As the tension of cable 30 is increased, first mating surface 160 interlocks with second mating surface 162 of an adjacent link 156 in the series to selectively fix links 156 in a selected orientation. Teeth 172, 174 become disposed in the grooves of the opposing mating surface to selectively fix a link 156 and an adjacent link 156 in a particular relative orientation such that arm 54 and surgical assembly 20 support an instrument in a position relative to a surgical site, according to the requirements of a particular application. Prior to interlocking fixation, link 156 is movable relative to an adjacent link 156 through an angle in a single plane only to provide reliability in operation and fixation of mating parts, similar to that described above. It is contemplated that the barrel shaped articulation of links 156 can also provide a full hinge motion in one plane and a limited hinge motion in a plane normal to the full hinge motion in one plane.

In one embodiment, as shown in FIGS. 12-15, arm 54 of surgical assembly 20, similar to that described above, includes a series of relatively movable links 256. Link 256 has a first end 280 having a cylindrical configuration and a second end 282 having a block configuration. Links 256 define an axial bore 258 configured for disposal of cable 30. Axial bore 258 is formed with each link 256 and has a rectangular configuration therethrough that decreases in width from first end 280 to second end 282. First end 280 defines a first mating surface 260 and second end 282 defines an opposing second mating surface 262, the mating surfaces being configured to interlock with a reciprocal mating surface of an adjacent link 256 in the series of links for support and positioning of an instrument, as described above. Axial bore 258 extends through mating surfaces 260,262 for disposal of cable 30.

Mating surfaces 260,262 include a plurality of teeth 272,274 and adjacent grooves disposed arcuately about the cylindrical surface that interlock, similar to that described above. As the tension of cable 30 is increased, first mating surface 260 interlocks with second mating surface 262 of an adjacent link 256 in the series to selectively fix links 256 in a selected orientation. Teeth 272, 274 become disposed in the grooves of the opposing mating surface to selectively fix a link 256 and an adjacent link 256 in a particular relative orientation such that arm 54 and surgical assembly 20 support an instrument in a position relative to a surgical site, according to the requirements of a particular application. Prior to interlocking fixation, link 256 is movable relative to an adjacent link 256 through an angle in a single plane only to provide reliability in operation and fixation of mating parts, similar to that described above.

Figure 16:
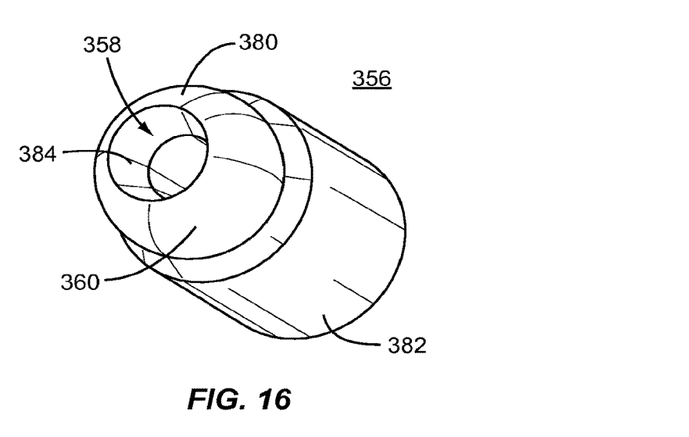
FIG. 16 is a perspective view of one embodiment of the link shown in FIG. 4.
Figure 17:
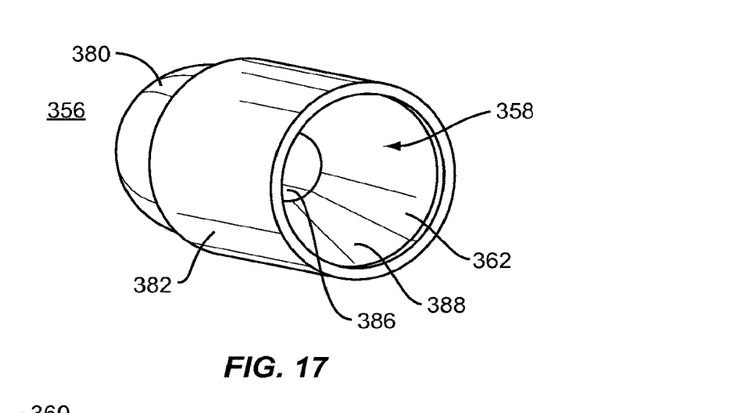
FIG. 17 is a perspective view of the link shown in FIG. 16.
Figure 18:
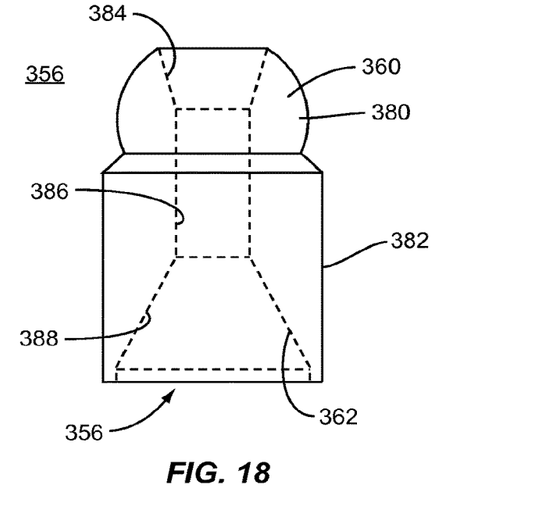
FIG. 18 is a side, cross section view of the link shown in FIG. 16.

In one embodiment, as shown in FIGS. 16-18, arm 54 of surgical assembly 20, similar to that described above, includes a series of relatively movable links 356. Link 356 has a first end 380 having a spherical dome configuration and a second end 382 having a cylindrical configuration. Links 356 define an axial bore 358 configured for disposal of cable 30. Each link 356 defines a first frustro-conical cavity 384, a cylindrical cavity 386 and a second frustro-conical cavity 388. Cavities 384,386,388 form a portion of axial bore 358 passing through each link 356 and support cable 30. This configuration provides spherical dome articulation at first end 360 and a conical socket for receiving the spherical dome of first end 360 at second end 382. Cavity 388 has a relatively larger dimension that cavity 384 to accommodate first end 360. Link 356 provides full multi-axial motion relative to an adjacent link 356 and greater locking strength upon fixation of arm 54, as described above.

First end 380 defines a first mating surface 360 and second end 382 defines an opposing second mating surface 362, the mating surfaces being configured to interlock with a reciprocal mating surface of an adjacent link 356 in the series of links for support and positioning of an instrument, as described above. Axial bore 358 extends through mating surfaces 360,362 for disposal of cable 30.

As the tension of cable 30 is increased, first mating surface 360 interlocks with second mating surface 362 of an adjacent link 356 in the series to selectively fix links 356 in a selected orientation. First mating surface 360 engages an opposing second mating surface 362 in a pressure and/or friction fit as links 356 are pulled together to selectively fix a link 356 and an adjacent link 356 in a particular relative orientation such that arm 54 and surgical assembly 20 support an instrument in a position relative to a surgical site, according to the requirements of a particular application.

Figure 19:
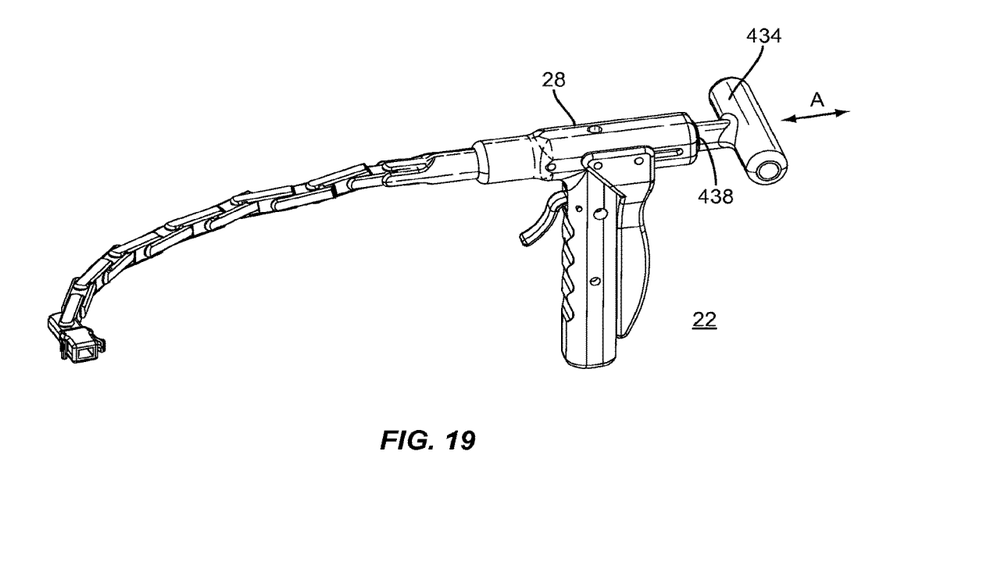
FIG. 19 is a perspective view of one embodiment of the tensioner shown in FIG. 2.

In one embodiment, as shown in FIG. 19, tensioner 22, similar to that described above, includes a first member, such as, for example, a t-handle 434. T-handle 434 is connected to body 28 and extends into body 28 through a slot 438. T-handle 434 is manipulable for tensioning cable 30, similar to slide 34 described above. T-handle 434 is axially movable, in the direction shown by arrows A through slot 438.

T-handle 434 includes an internal member (not shown) extending axially along the interior cavity of body 28 to engage a proximal end of the interlocking links. As the internal member of t-handle 434 engages the proximal end of the interlocking links, the proximal end of the interlocking links are urged/forced in the direction of arrows A according to the manipulation of t-handle 434. This engagement increases or decreases, depending on the direction of manipulation of t-handle 434 along arrows A, the tension of cable 30 due to the connection of cable 30 with body 28 and the distal end of the interlocking links, as described above. It is envisioned that t-handle 434 may include an internal member that is threaded with the interior cavity of body 28 such that t-handle 434 is rotatable or can be twisted for axial translation thereof and engagement with the proximal end of the links. In one embodiment, tensioner 22 has a first member, which includes slide 34 and t-handle 434, as shown in FIG. 19, for tensioning cable 30, as described above. For example, slide 34 may be employed to apply tension and t-handle 434 is used to provide fine adjustment.

Figure 20:
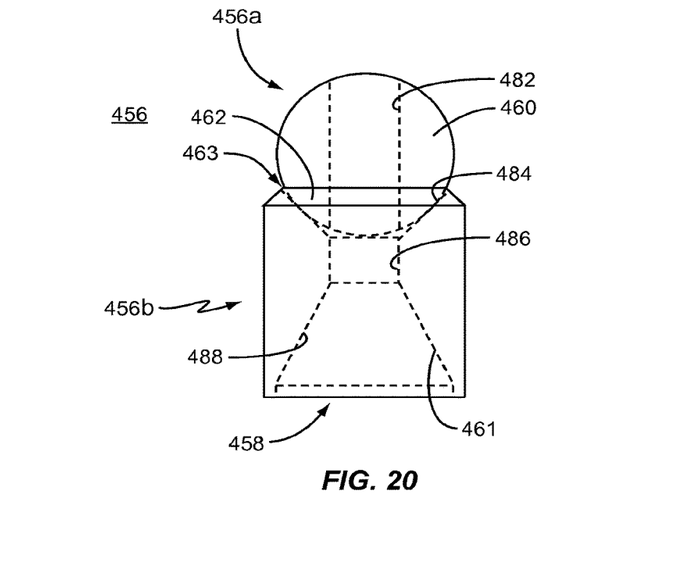
FIG. 20 is a side, cross section view of one embodiment of the links shown in FIG. 3.

In one embodiment, as shown in FIG. 20, arm 54 of surgical assembly 20, similar to that described above, includes a series of relatively movable links 456, which include a cannulated ball link 456a that is movable relative to a cylinder link 456b. Link 456a has a spherical configuration and link 456b has an elongated cylindrical configuration. Links 456 define an axial bore 458 configured for disposal of cable 30. Link 456a defines a cylindrical cavity 482. Link 456b defines a first frustro-conical cavity 484, a cylindrical cavity portion 486 and a second frustro-conical cavity 488. Cavities 482, 484,486,488 form a portion of axial bore 458 passing through links 456 and support cable 30. This configuration provides arcuate articulation cannulated ball link 456a and conical sockets, cavities 484, 488 for receiving link 456a.

Link 456a defines a mating surface 460 configured to interlock with a reciprocal mating surface 461 of link 456b and an opposing mating surface 462 configured to interlock with a reciprocal mating surface 463 of link 456b, in the series of links 456 for support and positioning of an instrument, as described above. Axial bore 458 extends through mating surfaces 460, 461, 462, 463 for disposal of cable 30.

As the tension of cable 30 is increased, mating surface 460 interlocks with mating surface 461 and mating surface 462 interlocks with mating surface 463 in the series to selectively fix links 456 in a selected orientation. The mating surfaces of links 456 engage in a pressure and/or friction fit as links 456 are pulled together to selectively fix a 456a and an adjacent link 456b in a particular relative orientation such that arm 54 and surgical assembly 20 support an instrument in a position relative to a surgical site, according to the requirements of a particular application.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical assembly comprising:
   a tensioner;
   an elastic cable coupled to the tensioner; and
   an arm extending from the tensioner and including a series of relatively moveable links that define an axial bore, the cable extending through the axial bores, each link defining a first mating surface and a second mating surface disposed in a configuration such that tensioning of the tension member interlocks the first mating surfaces with the second mating surfaces in the series to selectively fix the links in a selected orientation,
   wherein a distal one of the links comprises a mating surface configured to interlock with one of the second mating surfaces and an end defining a cavity configured for receiving a surgical instrument, and
   wherein the distal one of the links comprises a pair of pawls that are pivotable relative to a body of the distal one of the links from a first configuration in which a portion of each of the pawls is positioned within the cavity to a second configuration in which the portions are spaced apart from the cavity.

2. A surgical assembly as recited in claim 1, wherein the pawls are configured for releasably retaining the surgical instrument within the cavity.

3. A surgical assembly as recited in claim 1, wherein the first mating surfaces each have a convex configuration and the second mating surfaces each have a concave configuration.

4. A surgical assembly as recited in claim 1, wherein the first mating surfaces each have a spherical dome configuration and the second mating surfaces each define a frustro-conical cavity.

5. A surgical assembly as recited in claim 1, wherein each of the links defines a first frustro-conical cavity, a cylindrical cavity and a second frustro-conical cavity.

6. A surgical assembly as recited in claim 5, wherein the cylindrical cavity is positioned between the frustro-conical cavities.

7. A surgical assembly as recited in claim 5, wherein the first frustro-conical cavity extends through the first mating surface, the first mating surface having a spherical dome configuration, the second frustro-conical cavity having a maximum width that is greater than that of the first frustro-conical cavity.

8. A surgical assembly as recited in claim 1, wherein the tensioner includes a body and a slide relatively movable therefrom, the slide being connected to the body and configured for manipulation for tensioning the cable.

9. A surgical assembly as recited in claim 8, wherein the tensioner further includes a ratchet mechanism connected with the body and the slide, the body being selectively fixable with the ratchet mechanism.

10. A surgical assembly as recited in claim 9, wherein the tensioner further includes a trigger connected with the ratchet mechanism and configured for manipulation to fix and release the body with the ratchet mechanism.

11. A surgical assembly as recited in claim 9, wherein the ratchet mechanism extends from a front surface of the slide and passes through a slot of the body.

12. A surgical assembly as recited in claim 11, wherein the ratchet mechanism is a rack with serrations that engage or mesh with reciprocal grooves in the slot to selectively fix tension of the cable.

13. A surgical assembly as recited in claim 1, further comprising the surgical instrument, wherein the surgical instrument is a retractor assembly.

14. A surgical assembly as recited in claim 13, wherein the retractor assembly includes a bar having grooves that are inserted into the cavity.

15. A surgical assembly as recited in claim 14, wherein the pawls are disposed within the grooves such that the distal link releasably retains the retractor assembly.

16. A surgical assembly as recited in claim 1, wherein one of the pawls extends from a first side of the distal link and another one of the pawls extends from an opposite second side of the distal link.

17. A surgical assembly comprising:
a tensioner;
an elastic cable coupled to the tensioner; and
an arm extending from the tensioner and including a series of relatively moveable links that define an axial bore, the cable extending through the axial bores, the links comprising a first link having a spherical configuration and a second link having an elongated cylindrical configuration, the first links each comprising a first mating surface configured to interlock with a reciprocal second mating surface of one of the second links, the first links each comprising a third mating surface opposite the first mating surface configured to interlock with a reciprocal fourth mating surface of one of the second links, the fourth mating surface being positioned opposite the second mating surface,
wherein tensioning of the tension member interlocks the mating surfaces in the series to selectively fix the links in a selected orientation, and
wherein the tensioner further includes a ratchet mechanism connected with the body and the slide, the body being selectively fixable with the ratchet mechanism, the tensioner further including a trigger connected with the ratchet mechanism and configured for manipulation to fix and release the body with the ratchet mechanism, the ratchet mechanism extending from a front surface of the slide and passing through a slot of the body.

18. A surgical assembly as recited in claim 17, wherein the first links are cannulated balls and the second links each define a first frustro-conical cavity, a cylindrical cavity and a second frustro-conical cavity.

19. A surgical assembly as recited in claim 18, wherein the second frustro-conical cavity defines the second mating surface and the first frustro-conical cavity defines the fourth mating surface.

20. A surgical assembly comprising:
a tensioner;
an elastic cable coupled to the tensioner; and
an arm extending from the tensioner and including a series of relatively moveable links that define an axial bore, the cable extending through the axial bores, each link defining a first mating surface and a second mating surface disposed in a configuration such that tensioning of the tension member interlocks the first mating surfaces with the second mating surfaces in the series to selectively fix the links in a selected orientation, the first mating surfaces each having a spherical dome configuration and the second mating surfaces each defining a frustro-conical cavity,
wherein a distal one of the links comprises a mating surface configured to interlock with one of the second mating surfaces and an end defining a cavity configured for receiving a surgical instrument, the distal one of the links comprising a pair of pawls that are pivotable relative to a body of the distal one of the links from a first configuration in which a portion of each of the pawls is positioned within the cavity to a second configuration in which the portions are spaced apart from the cavity,
wherein the tensioner further includes a ratchet mechanism connected with the body and the slide, the body being selectively fixable with the ratchet mechanism, the tensioner further including a trigger connected with the ratchet mechanism and configured for manipulation to fix and release the body with the ratchet mechanism, the ratchet mechanism extending from a front surface of the slide and passing through a slot of the body.

* * * * *

UNITED STATES PATENT AND TRADEMARK OFFICE
CERTIFICATE OF CORRECTION

PATENT NO. : 10,238,409 B2
APPLICATION NO. : 15/220819
DATED : March 26, 2019
INVENTOR(S) : Mire et al.

Page 1 of 1

It is certified that error appears in the above-identified patent and that said Letters Patent is hereby corrected as shown below:

On the Title Page

In Item (71), under "Applicant", in Column 1, Line 1, delete "WARSAW ORTHOPEDIC INC.," and insert -- WARSAW ORTHOPEDIC, INC., --, therefor.

In the Specification

In Column 1, Line 8, delete "2010," and insert -- 2010, now Pat. No. 9,486,296, --, therefor.

In Column 7, Line 43, delete "may" and insert -- may be --, therefor.

In Column 9, Line 12, delete "first end 360" and insert -- first end 380 --, therefor.

In Column 9, Line 13, delete "first end 360" and insert -- first end 380 --, therefor.

In Column 9, Line 15, delete "first end 360." and insert -- first end 380. --, therefor.

Signed and Sealed this
Second Day of July, 2019

Andrei Iancu
*Director of the United States Patent and Trademark Office*